(12) United States Patent
Ohashi

(10) Patent No.: US 11,376,563 B2
(45) Date of Patent: Jul. 5, 2022

(54) ORGANOMETALLIC FRAMEWORK

(71) Applicant: TOYOTA JIDOSHA KABUSHIKI KAISHA, Toyota (JP)

(72) Inventor: Yoshio Ohashi, Susono (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 281 days.

(21) Appl. No.: 16/827,770

(22) Filed: Mar. 24, 2020

(65) Prior Publication Data
US 2020/0330956 A1    Oct. 22, 2020

(30) Foreign Application Priority Data

Apr. 22, 2019 (JP) .............................. JP2019-081138

(51) Int. Cl.
 *B01J 20/22* (2006.01)
 *B01D 53/26* (2006.01)
 (Continued)

(52) U.S. Cl.
 CPC ............ *B01J 20/226* (2013.01); *B01D 53/02* (2013.01); *B01D 53/261* (2013.01);
 (Continued)

(58) Field of Classification Search
 CPC ...... B01J 20/226; B01D 53/02; B01D 53/261; B01D 2253/204; B01D 2257/80;
 (Continued)

(56) References Cited

U.S. PATENT DOCUMENTS

2018/0133684 A1   5/2018   Chang et al.
2018/0280929 A1   10/2018  Ohashi

FOREIGN PATENT DOCUMENTS

JP    2017088542 A    5/2017
JP    2018080146 A    5/2018
(Continued)

OTHER PUBLICATIONS

Cadiau et al., Design of Hydrophilic Metal Organic Framework Water Adsorbents for Heat Reallocation, Adv. Mater. 2015, 27, 4775-4780.
(Continued)

*Primary Examiner* — Anita Nassiri-Motlagh
(74) *Attorney, Agent, or Firm* — Dickinson Wright PLLC

(57) ABSTRACT

The present invention provides a metal-organic framework which can both adsorb water vapor in low relative humidity and reduce the magnitude of the humidity difference between the adsorption humidity and the desorption humidity.

A metal organic framework wherein the metal ion is an aluminum ion, a first ligand is an organic compound ion consisting of a first heterocycle having two carboxyl groups, and a heteroatom composing the first heterocycle is present on the minor angle side of the angle created by the two carboxyl groups, a second ligand is different than the first ligand, is an organic compound ion consisting of a second heterocycle having two carboxyl groups, and a heteroatom composing the second heterocycle is present on the major angle side of the angle create by the two carboxyl groups, and a third ligand is different than the first ligand and the second ligand, is an organic compound ion having two carboxyl groups, and the first ligand, second ligand, and third ligand are present in a specific ratio.

7 Claims, 14 Drawing Sheets

(51) Int. Cl.
  *C07D 213/80* (2006.01)
  *C07D 307/68* (2006.01)
  *C07F 5/06* (2006.01)
  *B01D 53/02* (2006.01)
  *F25B 30/00* (2006.01)

(52) U.S. Cl.
  CPC ......... *C07D 213/80* (2013.01); *C07D 307/68* (2013.01); *C07F 5/069* (2013.01); *F25B 30/00* (2013.01); *B01D 2253/204* (2013.01); *B01D 2257/80* (2013.01)

(58) Field of Classification Search
  CPC ..... C07D 312/80; C07D 307/68; C07F 5/069; F25B 30/00
  USPC ........................................................ 502/401
  See application file for complete search history.

(56) References Cited

FOREIGN PATENT DOCUMENTS

| | | |
|---|---|---|
| JP | 2018-145274 A | 9/2018 |
| JP | 2018172320 A | 11/2018 |
| WO | 2016186454 A1 | 11/2016 |
| WO | 2019/010102 A1 | 1/2019 |
| WO | 2020112899 A1 | 6/2020 |

OTHER PUBLICATIONS

Reinsch et al., Structures, Sorption Characteristics, and Nonlinear Optical Properties of a New Series of Highly Stable Aluminum MOFs, Chem. Mater. 2013, 25, 17-26.

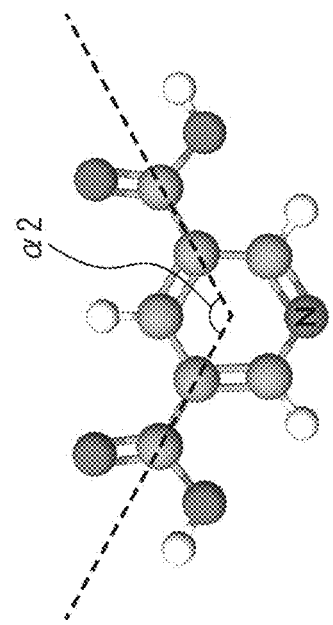
FIG. 3A H₂FDC
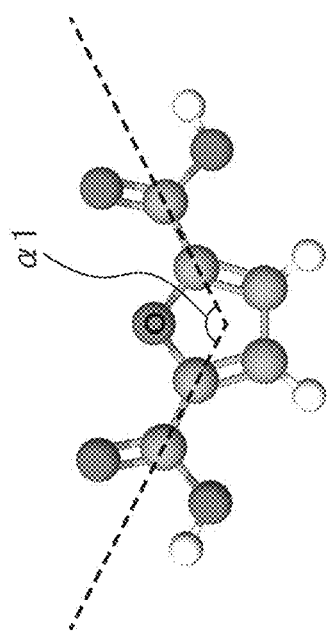
FIG. 3B H₂PyDC

ORGANOMETALLIC FRAMEWORK

FIELD

The present disclosure relates to an organometallic structure.

BACKGROUND

Metal-organic frameworks (MOF), which are porous compounds, are a type of material also called porous coordination polymers (PCP). MOFs have a coordinated network framework with a high surface area formed by the interaction of metal and organic ligands.

In recent years, a variety of research and development has been pursued in relation to these metal-organic frameworks.

For example, Patent Literature (PTL) 1 discloses an aluminum organic framework consisting of an $Al^{3+}$ ion coordinated to a first ligand derived from at least one type of aromatic dicarboxylic acid selected from isophthalic acid and derivatives thereof, and a second ligand derived from at least one type of heterocyclic dicarboxylic acid.

Also, Non-Patent Literature (NPL) 1 discloses an aluminum organic framework (CAU-10) of an $Al^{3+}$ ion and an isophthalate ion coordinated as a ligand.

Furthermore, NPL 2 discloses an aluminum organic framework of an $Al^{3+}$ ion, and a 2,5-furandicarboxylate ion coordinated as a ligand.

PTL 2 discloses a metal-organic framework having a tetravalent Group 4 elemental ion or a rare earth elemental ion as the metal ion, and having a molecular organic ion having a trimesic acid skeleton, and a molecular organic ion having an isophthalic acid skeleton as multidentate ligands.

In addition, PTL 3 discloses a metal-organic framework having, as the basic skeleton thereof, a framework represented by the formula $Me_6O_4(OH)_4(L)_6$ (Me is at least one metal atom selected from the group of Zr and Ti; and each L is a ligand coordinating to the metal atom Me), wherein the ligands L include a ligand derived from nitrogen-containing aromatic heterocyclic dicarboxylic acid and a ligand derived from aromatic dicarboxylic acid.

CITATION LIST

Patent Literature

[PTL 1] Japanese Unexamined Patent Publication (Kokai) No. 2018-080146
[PTL 2] Japanese Unexamined Patent Publication (Kokai) No. 2018-172320
[PTL 3] Japanese Unexamined Patent Publication (Kokai) No. 2017-088542

Non-Patent Literature

[NPL 1] H. Reinsch et al., "Structures, Sorption Characteristics, and Nonlinear Optical Properties of a New Series of Highly Stable Aluminum MOFs", Chem. Mater., 2013, 25, 17-26.
[NPL 2] A. Cadiau et al., "Design of Hydrophilic Metal Organic Framework Water Adsorbents for Heat Reallocation", Adv. Mater., 2015, 27, 4775-4780.

SUMMARY

Technical Problem

MOFs can adsorb water vapor, and therefore are considered for use as desiccants in chemical heat pumps and humidity control systems employed in automobiles, residences, and production equipment.

When a MOF is used as an adsorbing material, it is important that water vapor be adsorbed at a low relative humidity and that the magnitude of the humidity difference between the adsorption humidity and the desorption humidity be small.

However, many of the MOFs reported thus far have not been able to adsorb water vapor at low relative humidity, or have had a larger humidity difference between the adsorption humidity and the desorption humidity. Therefore, when these MOFs were used as desiccants in chemical heat pumps, the heat output was sometimes insufficient, or when these MOFs were used as desiccants in humidity control systems, the moisture removal performance was sometimes insufficient.

Therefore, out of consideration of the above circumstances, the object of the present disclosure is to provide a MOF that can achieve both adsorption of water vapor at a low relative humidity and a reduction in the magnitude of the humidity difference between the adsorption humidity and the desorption humidity.

Solution To Problem

The inventors of the present disclosure discovered through detailed examination that the above problems can be solved by the following means.

<Aspect 1>

A metal-organic framework comprising a metal ion, a first ligand, a second ligand, and an optional third ligand, wherein the metal ion is an aluminum ion, the first ligand is an organic compound ion consisting of a first heterocycle having two carboxyl groups, and a heteroatom composing the first heterocycle is present in the first ligand on the minor angle side of the angle created by the two carboxyl groups, the second ligand is different from the first ligand and is an organic compound ion having two carboxyl groups, and a heteroatom composing the second heterocycle is present in the second ligand on the major angle side of the angle created by the two carboxyl groups, the third ligand is an organic compound ion different from the first ligand and the second ligand and having two carboxyl groups, and relative to the total of the first ligand, the second ligand, and the third ligand, the first ligand is present in a percentage of more than 0 mol % to 70 mol %, the second ligand is present in a percentage of more than 0 mol % to 90 mol %, and the third ligand is present in a percentage of 0 mol % to 80 mol %.

<Aspect 2>

The metal-organic framework of Aspect 1, wherein the first heterocycle is a 5-membered ring or a 6-membered ring, and the second heterocycle is a 5-membered ring or a 6-membered ring.

<Aspect 3>

The metal-organic framework of Aspect 1 or 2, wherein the first heterocycle is a 5-membered ring, and the second heterocycle is a 6-membered ring.

<Aspect 4>

The metal-organic framework of any one of Aspects 1 to 3, wherein the first ligand is a 2,5-furandicarboxylate ion,
the second ligand is a 3,5-pyridinecarboxylate ion, and
the third ligand is an isophthalate ion.

<Aspect 5>

The metal-organic framework according to any one of Aspects 1 to 4, wherein the metal-organic framework has an adsorption humidity of not more than 11.5% and a difference between the adsorption humidity and a desorption humidity (adsorption humidity-desorption humidity) of not more than 3.0%, where the adsorption humidity is a humidity at which the amount of water vapor adsorbed is 70%, and the desorption humidity is a humidity at which the amount of water vapor adsorbed is 30%, when the amount of water vapor adsorbed at a relative humidity of 0 to 20% is taken to be 100%.

<Aspect 6>

A chemical heat pump having the metal-organic framework according to any one of Aspects 1 to 5 as a desiccant.

<Aspect 7>

A humidity control system having the metal-organic framework according to any one of Aspects 1 to 5 as a desiccant.

Advantageous Effects of Invention

According to the MOF of the present disclosure, adsorption of water vapor at a low relative humidity and a reduction in the magnitude of the humidity difference between the adsorption humidity and the desorption humidity can both be achieved simultaneously.

BRIEF DESCRIPTION OF DRAWINGS

FIG. 3A is a drawing showing the molecular structure of 2,5-furandicarboxylic acid ($H_2FDC$).

FIG. 3B is a drawing showing and the molecular structure of 3,5-pyridinedicarboxylic acid ($H_2PyDC$).

DESCRIPTION OF EMBODIMENTS

The present disclosure will be described below with reference to the drawings. The embodiments described below are examples of the present disclosure, and the present disclosure is not limited thereto.

«Metal-Organic Framework»

The MOF of the present disclosure is a metal-organic framework comprising a metal ion, a first ligand, a second ligand, and an optional third ligand, wherein the metal ion is an aluminum ion, the first ligand is an organic compound ion consisting of a first heterocycle having two carboxyl groups, and a heteroatom composing the first heterocycle is present in the first ligand on the minor angle side of the angle created by the two carboxyl groups, the second ligand is different from the first ligand and is an organic compound ion having two carboxyl groups, and a heteroatom composing the second heterocycle is present in the second ligand on the major angle side of the angle created by the two carboxyl groups, the third ligand is an organic compound ion different from the first ligand and the second ligand and having two carboxyl groups, and relative to the total of the first ligand, the second ligand, and the third ligand, the first ligand is present in a percentage of more than 0 mol % to 70 mol %, the second ligand is present in a percentage of more than 0 mol % to 90 mol %, and the third ligand is present in a percentage of 0 mol % to 80 mol %.

In the present disclosure, "heterocycle" refers to a saturated or unsaturated cyclic compound composed of two or more elements. It is preferable for the two or more elements to include a carbon atom and a heteroatom. In addition, a "heteroatom" is at least one atom selected from the group of an oxygen atom, a nitrogen atom, and a sulfur atom.

Additionally, the heterocyclic compound or the heterocyclic compound ion of the present disclosure includes derivates thereof substituted with suitable substituents as long as the effect of the present disclosure is not adversely affected. The substituent, as a group other than a carboxyl group, is not particularly limited, and can be at least one selected from the group consisting of, for example, a hydroxy group, a nitro group, a fluoro group, a chloro group, a bromo group, an iodo group, a cyano group, a methyl group, an ethyl group, a tert-butyl group, an ethynyl group, a carbonyl group, and an amino group.

In the present disclosure, "minor angle" refers to an angle from more than 0° to less than 180°. "Major angle" refers to an angle from 180° to less than 360°.

The reason that adsorption of water vapor at a low relative humidity and reducing of the size of the humidity difference between the adsorption humidity and the desorption humidity can both be achieved simultaneously according to the MOF of the present disclosure is not necessarily determined but is inferred to be the following.

Figure 1:
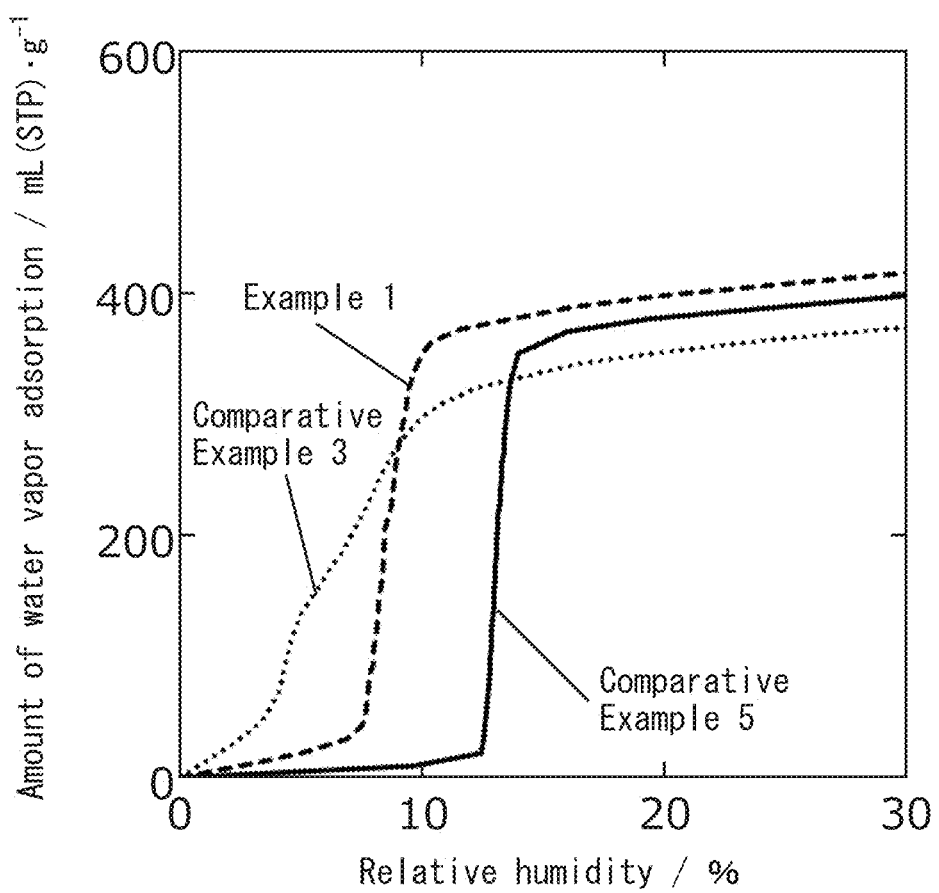
FIG. 1 is a graph showing the water vapor adsorption isotherms for the MOFs of Example 1, and Comparative Examples 1 and 3.

According to the keen research of the inventors of the present disclosure, in conventional MOFs such as the CAU-10 (corresponding to the MOF of Comparative Example 1 of the present disclosure) disclosed in NPL 1, which has an $Al^{3+}$ ion, and isophthalate ions coordinating as ligands, the magnitude of the humidity difference between adsorption humidities and desorption humidities is small, but the relative humidity at which water vapor adsorbed is high at around 13%, as shown in FIG. 1.

In contrast, in CAU-10-PyDC (corresponding to the MOF of Comparative Example 3 of the present disclosure) in which the ligands of CAU-10 were each replaced with a 3,5-pyridine dicarboxylate ion having two carboxyl groups, the water vapor adsorption relative humidity was lower than that of CAU-10, but the magnitude of the humidity difference between adsorption humidity and desorption humidity featured a water vapor adsorption isotherm with two levels and was much larger than that of CAU-10.

Figure 2:
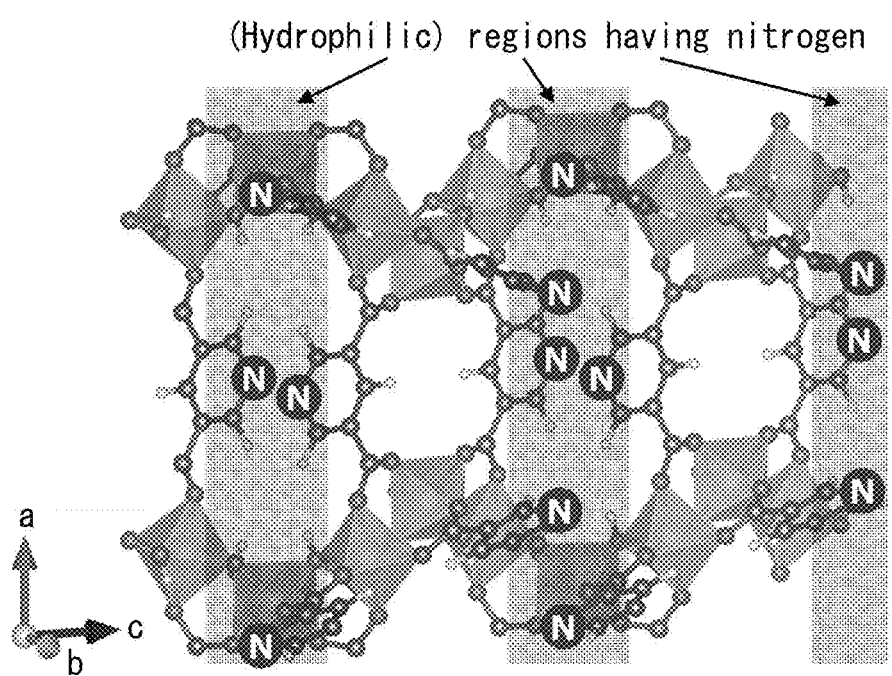
FIG. 2 is a drawing showing the pore structure of CAU-10-PyDC.

In addition, as shown in FIG. 2, in this CAU-10-PyDC microporous framework, it is clear that the region having a nitrogen atom and the region not having a nitrogen atom are clearly divided. The nitrogen atom has a lone pair of electrons such that it can form hydrogen bonds with water molecules, and therefore, in the microporous framework of CAU-10-PyDC, the "region having a nitrogen atom" is a region that is relatively hydrophilic, and the "region not having a nitrogen atom" is a region that is relatively hydrophobic. The reason that the water vapor adsorption isotherm for the CAU-10-PyDC of the above FIG. 1 has two levels is considered to be that in the microporous framework of CAU-10-PyDC, water vapor is adsorbed at a low relative humidity (about 4%) in the relatively hydrophilic region, and then water vapor is adsorbed at a high relative humidity (about 8%) in the relatively hydrophobic region.

Thus, the inventors of the present disclosure hypothesized that adjusting the balance of the hydrophilic region and the hydrophobic region in a new MOF microporous framework is important for achieving both adsorption of water vapor in low relative humidity and reducing the magnitude of the humidity difference between the adsorption humidity and the desorption humidity. The MOF of the present disclosure which the present inventors developed includes a first ligand, a second ligand, and an optional third ligand as mutually different ligands, wherein by including the specific structures of these ligands in a specific ratio, a balance between the hydrophilic regions and hydrophobic regions in the porous structure of the MOF can be achieved, whereby the effect of the present disclosure is demonstrated.

For example, by using a first ligand and a second ligand with different structures in combination in the MOF of Example 1 of the present disclosure shown in FIG. 1, the number of heteroatoms in the hydrophilic region can be reduced relative to the microporous framework of conventional CAU-10-PyDC, such that the hydrophilicity level is reduced, and the number of heteroatoms in the relatively hydrophobic region can be increased, such that the hydrophobicity level is reduced. Thus, the hydrophilicity level can be raised relatively evenly on the whole, such that a single level curve can be obtained for the water vapor adsorption isotherm.

Regarding the ligands with different structures, in the present disclosure, the first ligand is an organic compound ion consisting of a first heterocycle having two carboxyl groups, and in the first ligand, a heteroatom composing the first heterocycle is present on the minor angle side of the angle formed by the two carboxyl groups, and the second ligand is different from the first ligand, and is an organic compound ion consisting of a second heterocycle having two carboxyl groups, and in the second ligand, a heteroatom composing the second heterocycle is present on the major angle side of the angle formed by the two carboxyl groups.

For example, FIG. 3A is a drawing showing the molecular structure of 2,5-furandicarboxylic acid ($H_2FDC$) which can be used as the first ligand. As shown in FIG. 3A, in $H_2FDC$, the oxygen atom which is the heteroatom composing the furan ring is present on the minor angle side of the angle al formed by the two carboxyl groups. In addition, FIG. 3B is a drawing showing the molecular structure of 3,5-pyridinedicarboxylic acid ($H_2PyDC$) which can be used as the second ligand. As shown in FIG. 3B, in $H_2PyDC$, the nitrogen atom which is the heteroatom composing the pyridine ring is present on the major angle side of α2 formed by the two carboxyl groups.

As an example demonstrating the effect of the present disclosure, for example, the adsorption humidity of the MOF of the present disclosure can be not more than 11.5%, not more than 11.2%, not more than 11.0%, not more than 10.5%, or not more than 9.5%, and not less than 8.0%, and the difference between the adsorption humidity and the desorption humidity (adsorption humidity-desorption humidity) can be not more than 3.0%, not more than 2.9%, not more than 2.5%, not more than 2.0%, not more 1.5%, or not more than 1.0% and not less than 0.5%, where the adsorption humidity is a humidity at which the amount of water vapor adsorbed is 70%, and the desorption humidity is a humidity at which the amount of water vapor adsorbed is 30%, when the amount of water vapor adsorbed at a relative humidity of 0 to 20% is taken to be 100%.

The components constituting the MOF of the present disclosure will be explained in detail below.

<Metal Ion>

The metal ion used in the MOF of the present disclosure is an aluminum ion ($Al^{3+}$). In the MOF of the present disclosure, the aluminum coordinately bonds six oxygen atoms and forms an octahedral structure of $AlO_6$.

$AlO_6$ octahedra can include a helical structure $[Al(COO)_2 OH]_\infty$ sharing vertices in the cis form, and form, for example, a CAU-10-type MOF, or can include a straight $[Al(COO)_2OH]_\infty$ sharing vertices in the trans form and form, for example, a MIL-53-type MOF.

The source of aluminum ions is not particularly limited as long as the source includes aluminum atoms, and from the perspective of having a high solubility in water and polar solvents, can be, for example, at least one selected from the group consisting of aluminum chloride, aluminum nitrate, and aluminum sulfate. Also, as the aluminum ion source, the hydrates of compounds of the above aluminum ion sources can be used. More specifically, the hydrates of compounds of these aluminum ion sources can be, for example, aluminum chloride hexahydrate ($AlCl_3 \cdot 6H_2O$), aluminum nitrate nonahydrate ($Al(NO_3)_3 \cdot 9H_2O$), and aluminum sulfate tetradecahydrate to octadecahydrate ($Al_2(SO_4)_3 \cdot 14$-$18H_2O$), but are not limited thereto.

<First Ligand>

The first ligand used in the MOF of the present disclosure is an organic compound ion consisting of a first heterocycle having two carboxyl groups, and in the first ligand, the heteroatom constituting the first heterocycle is present on the minor angle side of the angle formed by the two carboxyl groups.

The number of atoms constituting the first heterocycle is not particularly limited, and can be, for example, not less than 3 and not more than 10. Thus, the first heterocycle can be a three-membered, four-membered, five-membered, six-membered, seven-membered, eight-membered, nine-membered, or ten-membered ring, and in particular, it is preferable that the first heterocycle be a five-membered or six-membered ring.

The first heterocycle can be a saturated heterocycle or can be an unsaturated heterocycle.

Preferably, the first heterocycle is an unsaturated heterocycle. Examples of this type of heterocycle include a pyrrole ring, a furan ring, a thiophene ring, a pyridine ring, a pyran ring, a thiapyran ring, an imidazole ring, a pyrazole ring, an oxazole ring, a thiazole ring, an imidazoline ring, or a pyridazine ring having two carboxyl groups, but are not limited thereto. In particular, the first heterocycle is preferably a pyran ring, a pyridine ring, a furan ring, or a thiophene having two carboxyl groups, and is most preferably a furan ring having two carboxyl groups.

The first ligand of the present disclosure is an organic compound ion having the above first heterocycle, wherein a heteroatom composing the first heterocycle is present on the minor angle side of the angle formed by the two carboxyl groups.

More specifically, the first ligand of the present disclosure can be a keridonate ion, chelidamate ion, a 2,6-pyridinedicarboxylate ion, a 2,5-furandicarboxylate ion, or a 2,5-thiophenedicarboxylate ion, but is not limited thereto. In particular, the first ligand is preferably a 2,5-furandicarboxylate ion. Also, as a source for the first ligand, the corresponding dicarboxylic acids for each can be used. For example, as the source for 2,5-furandicarboxylate ions, 2,5-furandicarboxylic acid can be used.

In the MOF of the present disclosure, relative to the total of the first ligand, the second ligand, and the third ligand, the first ligand is present in a percentage of more than 0 mol % to not more than 70 mol %. More specifically, relative to the total of the first ligand, the second ligand, and the third ligand, the first ligand can be more than 0 mol %, not less than 5 mol %, not less than 7 mol %, not less than 10 mol %, not less than 15 mol %, not less than 20 mol %, not less than 25 mol %, not less than 30 mol %, not less than 35 mol %, not less than 40 mol %, not less than 45 mol %, not less than 50 mol %, not less than 55 mol %, not less than 60 mol %, or not less than 65 mol %, and not more than 70 mol %, not more than 65 mol %, not more than 60 mol %, not more than 55 mol %, not more than 50 mol %, not more than 45 mol %, not more than 40 mol %, not more than 35 mol %, not more than 30 mol %, not more than 25 mol %, not more than 20 mol %, not more than 15 mol %, not more than 10 mol %, not more than 8 mol %, not more than 5 mol %, not more than 2 mol %, or not more than 1 mol %.

<Second Ligand>

The second ligand used in the MOF of the present disclosure is different from the first ligand above, and is an organic compound ion consisting of a second heterocycle having two carboxyl groups, and the heteroatom composing the second heterocycle is present in the second ligand on the major angle side of the angle formed by the two carboxyl groups.

The number of atoms constituting the second heterocycle is not particularly limited, and can be, for example, not less than 3 and not more than 10. Thus, the second heterocycle can be a three-membered, four-membered, five-membered, six-membered, seven-membered, eight-membered, nine-membered, or ten-membered ring, and in particular, it is preferable that the second heterocycle be a five-membered or six-membered ring. In addition, from the perspective of differentiating the first ligand and the second ligand, if the first heterocycle above is a five-membered ring for example, the second heterocycle is preferably a six-membered ring.

The second heterocycle can be a saturated heterocycle or can be an unsaturated heterocycle.

Preferably, the second heterocycle is an unsaturated heterocycle. Examples of this type of heterocycle include a pyrrole ring, a furan ring, a thiophene ring, a pyridine ring, a pyran ring, a thiapyran ring, an imidazole ring, a pyrazole ring, an oxazole ring, a thiazole ring, an imidazoline ring, or a pyridazine ring having two carboxyl groups, but are not limited thereto. In particular, the second heterocycle is preferably a pyran ring, a pyridine ring, a furan ring, or a thiophene having two carboxyl groups, and is most preferably a pyridine ring having two carboxyl groups.

The second ligand of the present disclosure is an organic compound ion having the above second heterocycle, wherein a heteroatom constituting the second heterocycle is present on the major angle side of the angle formed by the two carboxyl groups.

More specifically, the second ligand of the present disclosure can be a 3,5-pyridinedicarboxylate ion, a 2,4-pyridinedicarboxylate ion, or a pyrazole-3,5-dicarboxylate ion, but is not limited thereto. In particular, the second ligand is preferably a 3,5-pyridinedicarboxylate ion. Further, as a source for the second ligand, the corresponding dicarboxylic acids for each can be used. For example, as the source for 3,5-pyridinedicarboxylate ions, 3,5-pyridinedicarboxylic acid can be used.

In the MOF of the present disclosure, relative to the total of the first ligand, the second ligand, and the third ligand, the second ligand is present in a percentage of more than 0 mol % to not more than 90 mol %. More specifically, relative to the total of the first ligand, the second ligand, and the third ligand, the second ligand can be more than 0 mol %, not less than 5 mol %, not less than 7 mol %, not less than 10 mol %, not less than 15 mol %, not less than 20 mol %, not less than 25 mol %, not less than 30 mol %, not less than 35 mol %, not less than 40 mol %, not less than 45 mol %, not less than 50 mol %, not less than 55 mol %, not less than 60 mol %, not less than 65 mol %, not less than 70 mol %, not less than 75 mol %, not less than 80 mol %, or not less than 85 mol %, and not more than 90 mol %, not more than 85 mol %, not more than 80 mol %, not more than 75 mol %, not more than 70 mol %, not more than 65 mol %, not more than 60 mol %, not more than 55 mol %, not more than 50 mol %, not more than 45 mol %, not more than 40 mol %, not more than 35 mol %, not more than 30 mol %, not more than 25 mol %, not more than 20 mol %, not more than 15 mol %, not more than 10 mol %, not more than 8 mol %, not more than 5 mol %, not more than 2 mol %, or not more than 1 mol %.

<Third Ligand>

The MOF of the present disclosure may optionally include a third ligand. The optionally included third ligand is different from both the first ligand and the second ligand above, and is an organic compound ion having two carboxyl groups.

The optionally included third ligand can be, for example, an isophthalate ion, a 1,3-cyclohexanedicarboxylate ion, a glutarate ion, a terephthalate ion, an oxalate ion, a fumarate ion, a malonate ion, a trans,trans-muconate ion, a cis,cis-muconate ion, a 2,6-naphthalenedicarboxylate ion, a 9,10-anthracene dicarboxylate ion, a 2,2'-diamino-4,4'-stilbene dicarboxylate ion, a 2,2'-dinitro-4,4'-stilbene dicarboxylate ion or a 2,3-pyrazinedicarboxylate ion, but is not limited thereto. In particular, the optionally included third ligand is preferably an isophthalate ion. Also, as a source for the third ligand, the corresponding dicarboxylic acids for each can be used. For example, as the source of isophthalate ions, isophthalic acid can be used.

In the MOF of the present disclosure, relative to the total of the first ligand, the second ligand, and the third ligand, the third ligand is present in a percentage of not less than 0 mol % to not more than 80 mol %. More specifically, relative to the total of the first ligand, the second ligand, and the third ligand, the third ligand can be not less than 0 mol %, not less than 5 mol %, not less than 7 mol %, not less than 10 mol %, not less than 15 mol %, not less than 20 mol %, not less than 25 mol %, not less than 30 mol %, not less than 35 mol %, not less than 40 mol %, not less than 45 mol %, not less than 50 mol %, not less than 55 mol %, not less than 60 mol %, not less than 65 mol %, not less than 70 mol %, or not less than 75 mol %, and not more than 80 mol %, not more than 75 mol %, not more than 70 mol %, not more than 65 mol %, not more than 60 mol %, not more than 55 mol %, not more than 50 mol %, not more than 45 mol %, not more than 40 mol %, not more than 35 mol %, not more than 30 mol %, not more than 25 mol %, not more than 20 mol %, not more than 15 mol %, not more than 10 mol %, not more than 8 mol %, not more than 5 mol %, not more than 2 mol %, or not more than 1 mol %.

«Method for Manufacturing a Metal-Organic Framework»

The metal-organic framework of the present invention can be manufactured using, for example, a hydrothermal synthesis method or a solvothermal synthesis method.

More specifically, the metal-organic framework of the present disclosure can be manufactured by heating a raw material solution including an aluminum ion source as the metal ion source, a first ligand source, a second ligand source, an optional third ligand source, and a solvent to cause a reaction.

The concentration of aluminum ions included in the raw material solution is not particularly limited, and can be, relative to the solvent, not less than 10 mmol/L, not less than 25 mmol/L, not less than 50 mmol/L, not less than 75 mmol/L, not less than 100 mmol/L, not less than 125 mmol/L, not less than 150 mmol/L, not less than 175 mmol/L, not less than 200 mmol/L, not less than 225 mmol/L, not less than 250 mmol/L, or not less than 300 mmol/L, and not more than 500 mmol/L, not more than 400 mmol/L, not more than 300 mmol/L, or not more than 250 mmol/L.

The respective concentrations of the first ligand, the second ligand, and the optional third ligand included in the raw material solution is not particularly limited, and can be, relative to the solvent, not less than 10 mmol/L, not less than 20 mmol/L, not less than 30 mmol/L, not less than 40 mmol/L, not less than 50 mmol/L, not less than 60 mmol/L, not less than 70 mmol/L, not less than 80 mmol/L, not less than 90 mmol/L, not less than 100 mmol/L, not less than 150 mmol/L, or not less than 300 mmol/L, and not more than 300 mmol/L, not more than 250 mmol/L, or not more than 200 mmol/L.

In addition, the composition ratios of the first ligand source, the second ligand source and the third ligand source are not particularly limited as long as the first ligand, the second ligand, and the third ligand are obtained in the aforementioned composition range specific to each.

For example, relative to the total composition amount (mol) of the first ligand, the second ligand, and the optional third ligand, the first ligand source can be more than 0 mol % and less than 100 mol %, not less than 5 mol % and not more than 85 mol %, or not less than 10 mol % and not more than 80 mol %, the second ligand source can be more than 0 mol % and less than 90 mol %, not less than 5 mol % and not more than 85 mol %, or not less than 10 mol % and not more than 80 mol %, and the third ligand source can be not less than 0 mol % and less than 100 mol %, not less than 5 mol % and not more than 70 mol %, or not less than 10 mol % and not more than 60 mol %.

The solvent can be, for example, N,N-dimethylformaldehyde (DMF), N,N-diethylformamide (DEF), formic acid, acetic acid, methanol, ethanol, water or a mixture thereof, but is not limited thereto.

When heating, the raw material solution can be placed into a closed container and the heating can be performed under reflux of the raw material solution.

The heating temperature is not particularly limited, and can be, for example, not less than 100° C. or not less than 120° C. from the perspective of raising reactivity, and can be not more than 150° C. from the perspective of preventing vapor leaks during the reaction.

The heating time is not particularly limited and can be appropriately adjusted in conjunction with the heating temperature. The heating time can be, for example, not less than 6 hours, not less than 10 hours, not less than 12 hours, not less than 18 hours, not less than 24 hours, not less than 30 hours, not less than 36 hours, not less than 42 hours, not less than 48 hours, not less than 54 hours, or not less than 60 hours, and not more than 96 hours, not more than 84 hours, not more than 72 hours, not more than 60 hours, not more than 48 hours, not more than 24 hours, not more than 12 hours, or not more than 10 hours.

After the reaction is completed, the obtained product can be post-treated as appropriate.

The post-treatment can be, for example, filtering of the obtained product. In addition, as necessary, a poor solvent can be added to the filter cake obtained by filtering, and after dispersing the filter cake at room temperature or with appropriate heating, the filter cake can be filtered again. The poor solvent can be a solvent in which the target MOF does not dissolve readily, such as water, acetonitrile, hexane, or ethanol. Also, the temperature in the case of heating can be, for example, not less than 40° C., not less than 50° C., not less than 60° C., not less than 70° C., or not less than 80° C., and not more than 100° C., not more than 90° C., or not more than 80° C. The heating time in the case of heating can be, for example, not less than 1 hour, not less than 2 hours, not less than 6 hours, not less than 10 hours, or not less than 12 hours, and not more than 24 hours, or not more than 16 hours.

Further, by appropriately drying the filter cake obtained from filtration or re-filtration, the target MOF can be obtained. Drying can be performed under normal pressure, or under reduced pressure, but from the perspective of improving efficiency, it is preferable to perform drying under reduced pressure. Moreover, the temperature in the case of drying can be, for example, not less than 20° C., not less than 25° C., not less than 40° C., not less than 50° C., or not less than 60° C., and not more than 100° C., not more than 90° C., not more than 80° C., or not more than 60° C. The drying time in the case of drying can be, for example, not less than 1 hour, not less than 2 hours, not less than 6 hours, not less than 10 hours, or not less than 12 hours, and not more than 24 hours or not more than 16 hours.

«Chemical Heat Pump»

The metal-organic framework of the present disclosure can be used, for example, as a desiccant in a chemical heat pump. The chemical heat pump in such cases has a water reservoir for storing water as a working medium, a desiccant holder for holding the desiccant, and a water vapor channel that allows water vapor to flow between the water reservoir and the desiccant holder. Regarding the chemical heat pump, the water reservoir may be used as both an evaporator and a condenser, or the water reservoir can be used as an evaporator and condensation of the water vapor can be performed by a separate condenser. Such chemical heat pumps can be used for cooling or heating in automobiles, residences, and production equipment.

Figure 13A:
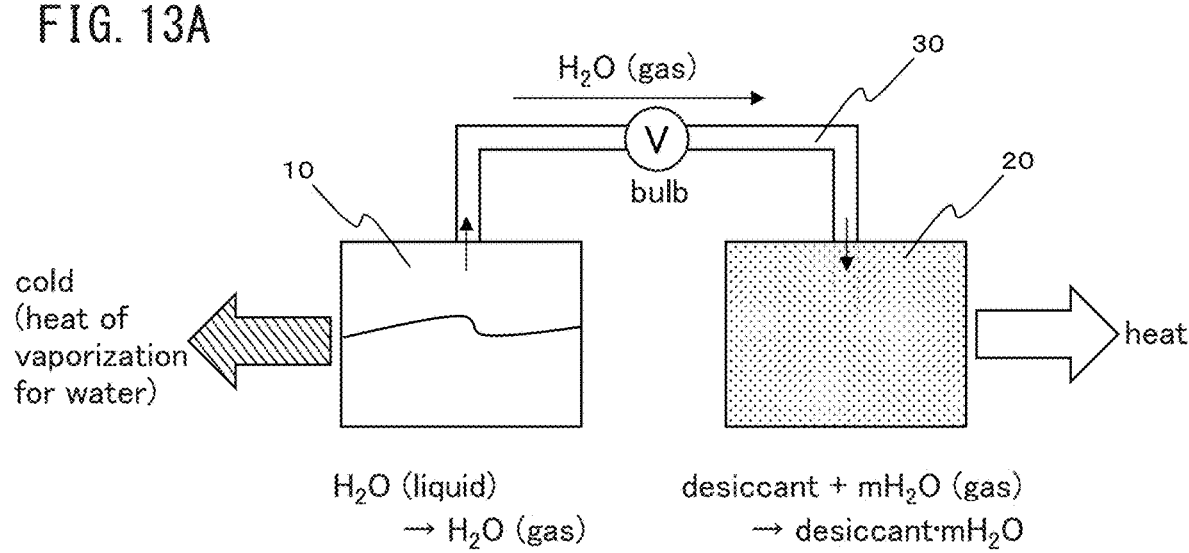
FIG. 13A is a schematic drawing of a heat pump that uses the MOF of the present disclosure.

An aspect when the water reservoir of the chemical pump is used as both an evaporator and a condenser is explained. For example, as shown on the left side of FIG. 13A, heat from the outside is supplied to the water ($H_2O$ (liquid)) of water reservoir 10 to evaporate the water of the water reservoir into water vapor ($H_2O$ (gas)). This stage can also be considered to be supplying cold from the water reservoir to the outside by evaporating the water in the water reservoir to form water vapor. In this kind of chemical pump, as shown on the right side of FIG. 13A, the water vapor generated at water reservoir 10 is passed through the water vapor channel 30 and supplied to the desiccant holder 20, and then reacted with the desiccant such that the heat of adsorption is supplied to the outside. Essentially, this type of pump can transfer heat from the water reservoir 10 side to the desiccant holder 20 side.

Figure 13B:
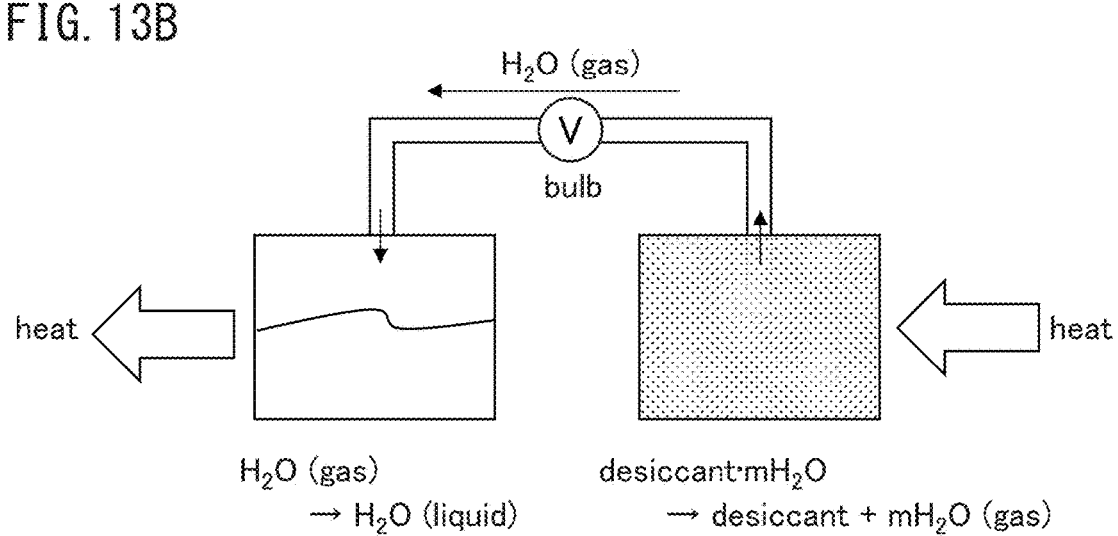
FIG. 13B is a schematic drawing of a heat pump that uses the MOF of the present disclosure.

Also, in this type of chemical heat pump, during the regeneration stage which enables the reaction shown in FIG. 13A to be performed again, as shown on the right side of FIG. 13B, heat is supplied from the outside to the desiccant holder 20 to separate the water from the desiccant and form water vapor. This stage can also be considered to be supplying cold from the desiccant holder 20 to the outside by separating water from the desiccant of the desiccant holder 20. In this kind of chemical pump, as shown on the left side of FIG. 13B, the water vapor generated at the desiccant holder 20 is supplied to the water reservoir and then liquified such that the latent heat of condensation is supplied to the outside.

«Humidity Control System»

The metal-organic framework of the present disclosure can be used, for example, as a desiccant for a humidity control system. The humidity control system in such cases has a desiccant holder for holding a desiccant, an air supply channel for supplying air containing water vapor to the desiccant holder, and an air extraction channel for removing air supplied to the desiccant holder from the desiccant holder. Such humidity control systems can be used to dehumidify or control the humidity in automobiles, residences, and production equipment.

Figure 14A:
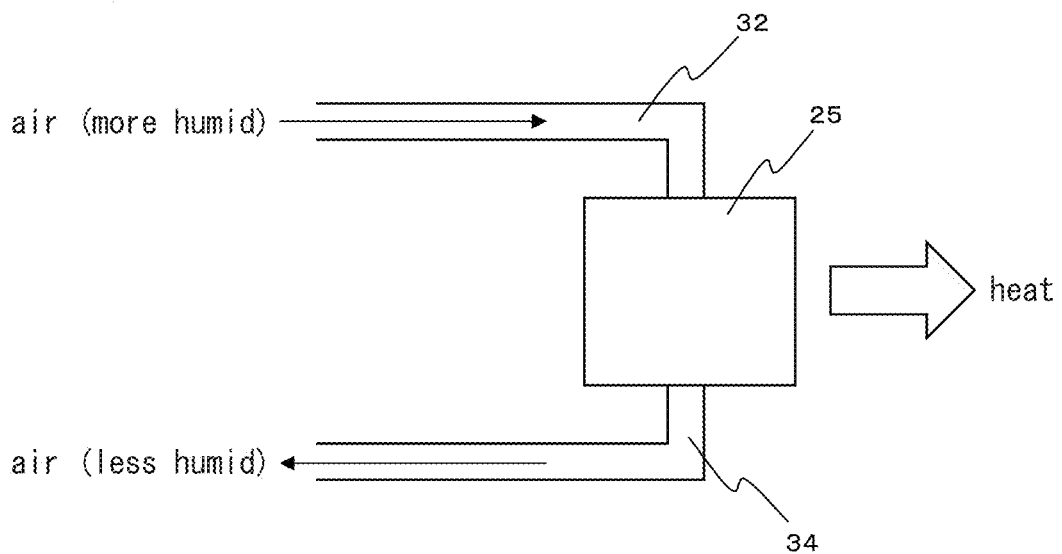
FIG. 14A is a schematic drawing of a humidity control system that uses the MOF of the present disclosure.

In this kind of humidity control system, as shown in FIG. 14A for example, air containing a relatively large amount of water vapor is passed from the outside through the air supply channel 32 and supplied to the desiccant holder 25, and then at least a portion of the water vapor in the air is adsorbed by the desiccant and removed from the air within the desiccant holder 25. At this time, the heat of adsorption is generated by adsorption of water vapor at the desiccant holder 25. Thereafter, at least a portion of the water vapor is removed within the desiccant holder 25 and the air with relatively less water vapor is passed through the air extraction channel 34 and removed from the desiccant holder. The phrases "relatively less water vapor" and "relatively large amount of water vapor" have meanings relative to each other, such that the "air with relatively less water vapor" means air with less water vapor in comparison to the "air with a relatively large amount of water vapor".

Figure 14B:
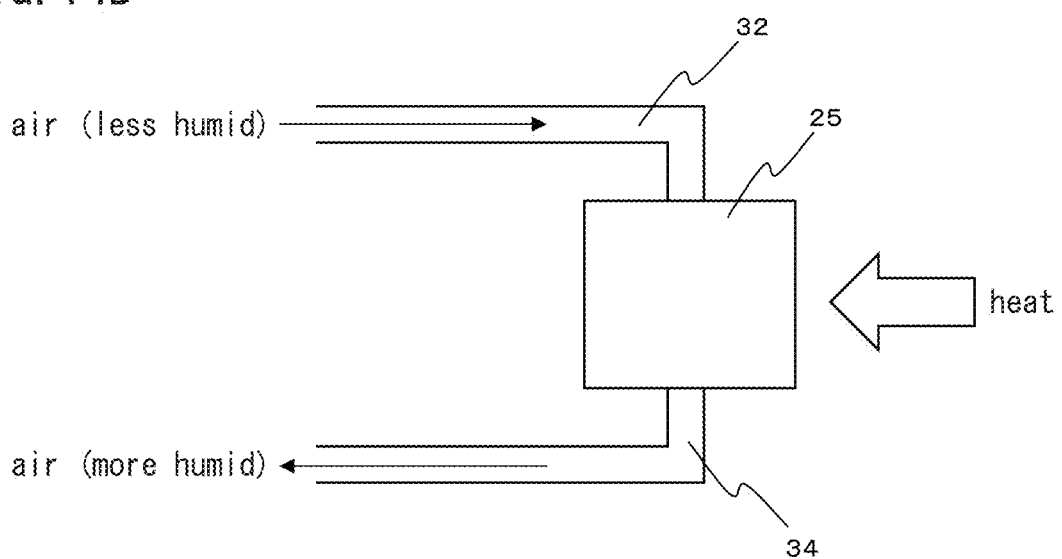
FIG. 14B is a schematic drawing of a humidity control system that uses the MOF of the present disclosure.

Also, in this kind of humidity control system, during the regeneration stage which enables the reaction shown in FIG. 14A to be performed again, as shown in FIG. 14B, while heat is supplied from the outside to the desiccant holder 20, air with relatively less water vapor is passed from the outside through the air supply channel 32 and supplied to the desiccant holder 25, whereby at least a portion of water vapor adsorbed by the desiccant in the desiccant holder 25 is removed and released into the air. Thereafter, the air with a relatively higher amount of water vapor due to the addition of water vapor in the desiccant holder 25 is removed from the desiccant holder through the air extraction channel 34. This regeneration stage can also be performed as a stage for performing humidification of the air. This regeneration stage can be performed with the flow of air in reverse, that is, air is introduced from the air extraction channel 34, and then, air can be extracted from the air supply channel 32. As above, the phrases "relatively less water vapor" and "relatively higher amount of water vapor" have meanings relative to each other.

EXAMPLES

The present disclosure will be described in detail below using Examples. However, the scope of the present disclosure is not limited thereto.

«Synthesis of Metal-Organic Frameworks (MOFs)»

The metal-organic frameworks (MOFs) of the Examples and Comparative Examples were synthesized using the reagents indicated in Table 1.

TABLE 1

| Reagent name | Chemical formula or abbreviated name | Vendor |
| --- | --- | --- |
| Aluminum chloride hexahydrate | $AlCl_3 \cdot 6H_2O$ | FUJIJFILM Wako Pure Chemical Corporation |
| 3,5-pyridinedicarboxylic acid | $H_2PyDC$ | Tokyo Chemical Industry Co., Ltd. |
| 2,5-furandicarboxylic acid | $H_2FDC$ | Tokyo Chemical Industry Co., Ltd. |
| Isophthalic acid | $H_2BDC$ | Tokyo Chemical Industry Co., Ltd. |
| N,N-dimethylformamide | DMF | Wako Pure Chemical Industries Ltd. |

Example 1

(1) 0.87 g (240 mmol/L) of $AlCl_3.6H_2O$ as a metal source, 0.28 g (120 mm/L) or $H_2FDC$ as a first ligand source, 0.30 g (120 mmol/L) of $H_2PyDC$ as a second ligand source, and 3 mL of DMF and 12 mL of water as a solvent were added into a 25 ml PTFE container (HUT-25, San-Ai Kagaku Co.)

(2) The PTFE container was placed in a pressure-resistant stainless steel outer cylinder (HUS-25, San-Ai Kagaku Co.) and heated at 120° C. for 48 hours.

(3) The precipitate of the generated product was filtered, dispersed in 100 mL of distilled water, heated overnight at 70° C., re-filtered, and the precipitate thereof was collected.

(4) The precipitate was heated to 60° C. overnight and dried while being depressurized to $10^{-1}$ Pa or lower to obtain the MOF of Example 1.

Example 2

The MOF of Example 2 was obtained in a manner similar to Example 1, except that 0.11 g (48 mmol/L) of $H_2FDC$ as a first ligand source, 0.48 g (192 mmol/L) as a second ligand source were used.

Example 3

The MOF of Example 3 was obtained in a manner similar to Example 1, except that 0.11 g (48 mmol/L) of $H_2FDC$ as a first ligand source, 0.12 g (48 mmol/L) of $H_2PyDC$ as a second ligand source, and 0.36 g (144 mmol/L) of $H_2BDC$ as a third ligand source were used.

Example 4

The MOF of Example 4 was obtained in a manner similar to Example 1, except that 0.17 g (72 mmol/L) of $H_2FDC$ as a first ligand source, 0.18 g (72 mmol/L) of $H_2PyDC$ as a second ligand source, and 0.24 g (96 mmol/L) of $H_2BDC$ as a third ligand source were used.

Example 5

The MOF of Example 5 was obtained in a manner similar to Example 1, except that 0.22 g (96 mmol/L) of $H_2FDC$ as a first ligand source, 0.24 g (96 mmol/L) of $H_2PyDC$ as a second ligand source, and 0.12 g (48 mmol/L) of $H_2BDC$ as a third ligand source were used.

Example 6

The MOF of Example 6 was obtained in a manner similar to Example 1, except that 0.34 g (144 mmol/L) of $H_2FDC$ as a first ligand source, 0.12 g (48 mmol/L) of $H_2PyDC$ as a second ligand source, and 0.12 g (48 mmol/L) of $H_2BDC$ as a third ligand source were used.

Example 7

The MOF of Example 7 was obtained in a manner similar to Example 1, except that 0.11 g (48 mmol/L) of $H_2FDC$ as a first ligand source, 0.36 g (144 mmol/L) of $H_2PyDC$ as a second ligand source, and 0.12 (48 mmol/L) of $H_2BDC$ as a third ligand source were used.

Example 8

The MOF of Example 8 was obtained in a manner similar to Example 1, except that 0.45 g (192 mmol/L) of $H_2FDC$ as a first ligand source, 0.06 g (24 mmol/L) of $H_2PyDC$ as a second ligand source, and 0.06 g (24 mmol/L) of $H_2BDC$ as a third ligand source were used.

Example 9

The MOF of Example 9 was obtained in a manner similar to Example 1, except that 0.06 g (24 mmol/L) of $H_2FDC$ as a first ligand source, 0.48 g (192 mmol/L) of $H_2PyDC$ as a second ligand source, and 0.06 g (24 mmol/L) of $H_2BDC$ as a third ligand were used.

Comparative Example 1

The MOF of Comparative Example 1 was obtained in a manner similar to Example 1, except that instead of a first ligand source and a second ligand source, 0.60 g (240 mmol/L) of $H_2BDC$ was used as a ligand source.

Comparative Example 2

The MOF of Comparative Example 2 was obtained in a manner similar to Example 1, except that instead of a first ligand source and a second ligand source, 0.56 g (240 mmol/L) of $H_2FDC$ was used as a ligand source.

Comparative Example 3

The MOF of Comparative Example 3 was obtained in a manner similar to Example 1, except that instead of a first ligand source and a second ligand source, 0.60 g (240 mmol/L) of $H_2PyDC$ was used as a ligand source.

Comparative Example 4

The MOF of Comparative Example 4 was obtained in a manner similar to Example 1, except that 0.51 g (216 mmol/L) of $H_2FDC$ as a first ligand source and 0.06 g (24 mmol/L) of $H_2PyDC$ as a second ligand source were used.

Comparative Example 5

The MOF of Comparative Example 5 was obtained in a manner similar to Example 1, except that 0.45 g (192 mmol/L) of $H_2FDC$ as a first ligand source and 0.12 g (48 mmol/L) of $H_2PyDC$ as a second ligand source were used.

Comparative Example 6

The MOF of Comparative Example 6 was obtained in a manner similar to Example 1, except that 0.06 g (24 mmol/L) of $H_2FDC$ as a first ligand source and 0.54 g (216 mmol/L) of $H_2PyDC$ as a second ligand source were used.

Comparative Example 7

The MOF of Comparative Example 7 was obtained in a manner similar to Example 1, except that 0.06 g (24 mmol/L) of $H_2FDC$ as a first ligand source, 0.06 g (24 mmol/L) of $H_2PyDC$ as a second ligand source, and 0.48 g (192 mmol/L) of $H_2BDC$ as a third ligand source were used.

<Measurement of X-Ray Diffraction (Confirmation of MOF Crystal Structure)>

X-ray diffraction was measured for each of the MOFs synthesized for the Examples and Comparative Examples. The measurement device and measurement conditions were as follows:

Measurement device: RINT RAPID II (Rigaku Corporation)
Measurement conditions: voltage 50 V, current 100 mA, collimator diameter ϕ0.3, sample angle ω5°.

Figure 4:
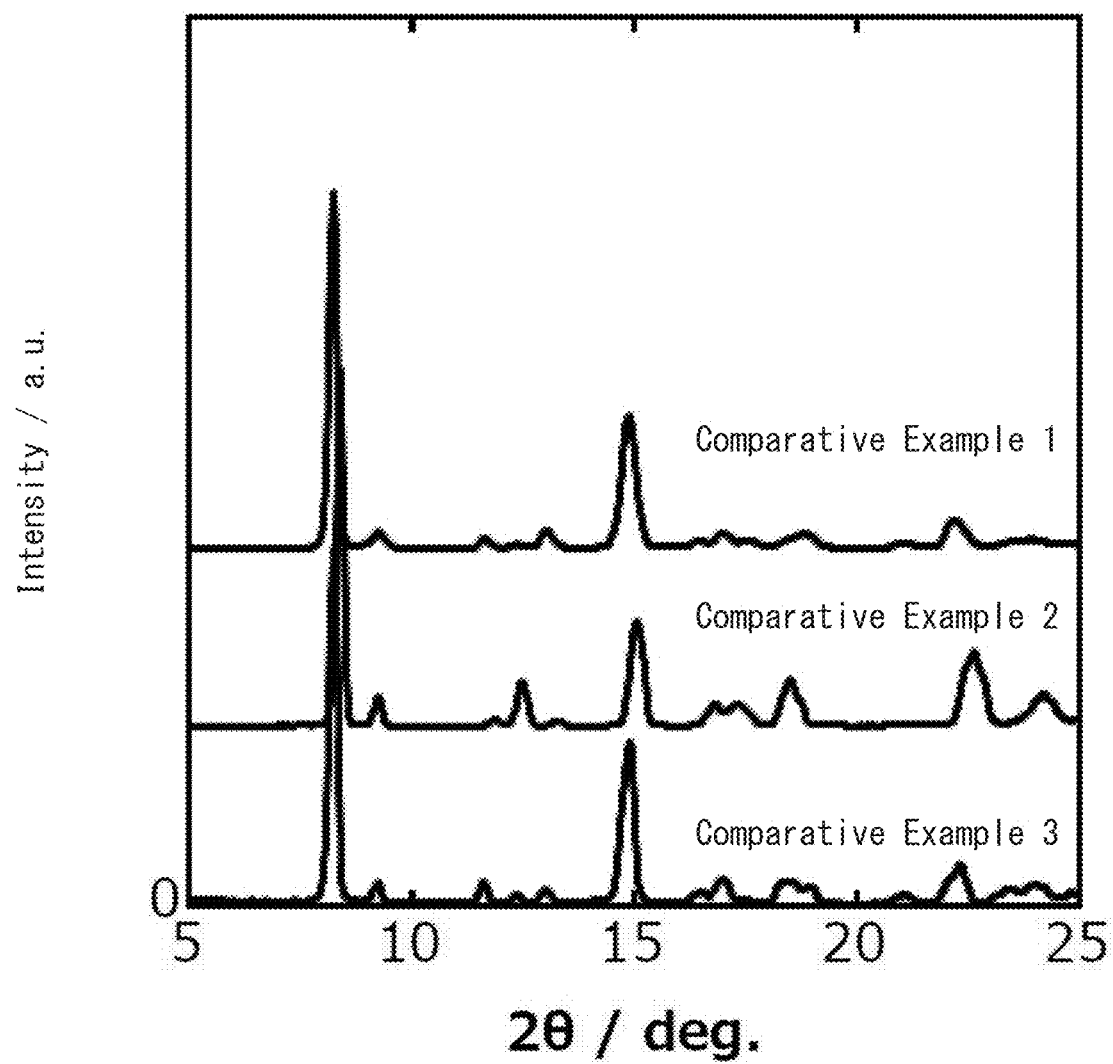
FIG. 4 is a graph showing X-ray diffraction patterns from the collective data for Comparative Examples 1 to 3.
Figure 5:
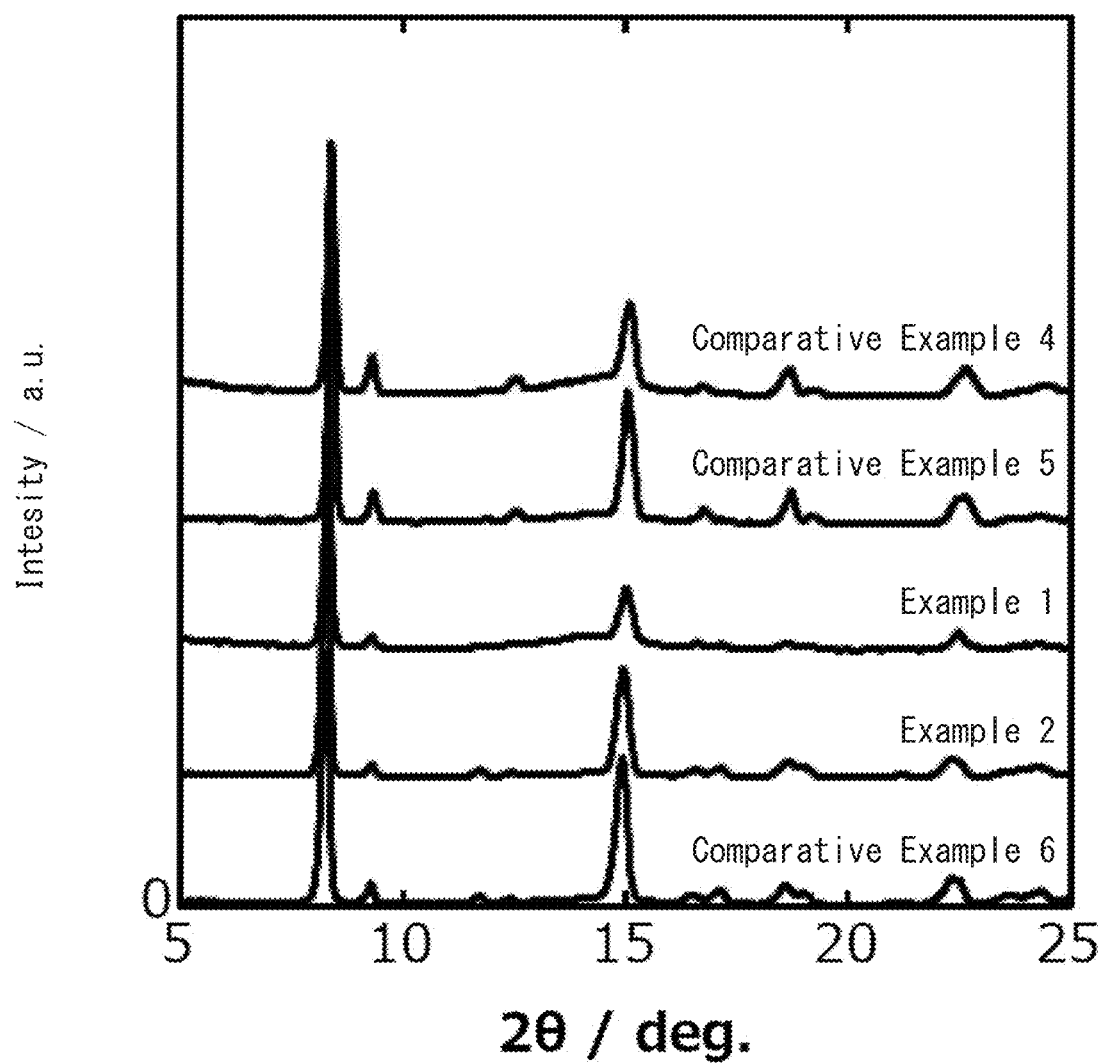
FIG. 5 is a graph showing X-ray diffraction patterns from the collective data for Examples 1 and 2, and Comparative Examples 4 to 6.
Figure 6:
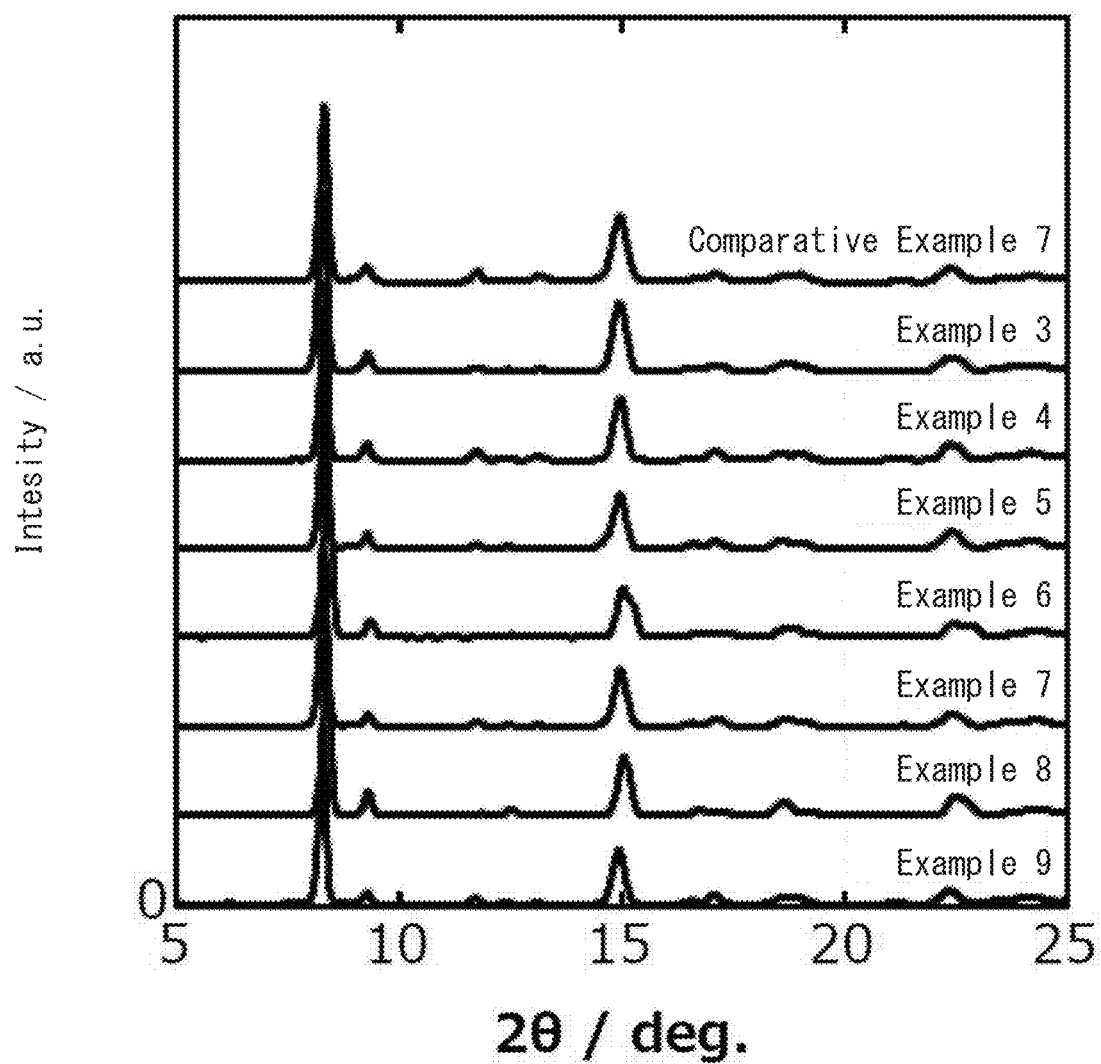
FIG. 6 is a graph showing X-ray diffraction patterns from the collective data for Examples 3 to 9 and Comparative Example 7.

FIGS. 4 to 6 show the X-ray diffraction patterns measured and obtained for the MOFs of each of the Examples and Comparative Examples.

<$^1$H-NMR Measurement (MOF Composition Analysis)>

The MOFs synthesized for each of the Examples and Comparative Examples were each decomposed, and thereafter the $^1$H-NMR spectra of the solutions thereof were measured, and the ratio of each ligand contained in the MOF was obtained from the integral ratio. The decomposition conditions, measurement device, and measurement conditions were as follows:

Decomposition conditions: MOF decomposed in 5 wt % solution of sodium hydroxide (NaOH) in heavy water ($D_2O$)

Measurement device: JNM-AL400 (JEOL, Ltd.)

Measurement conditions: measured the $^1$H-NMR spectrum of the solution using sodium 3-(trimethylsilyl)propionate-$d_4$ (TSP-$d_4$) as an internal standard.

<Measurement of Adsorption-Desorption of Water Vapor (Evaluation of Water Vapor Adsorption-Desorption Characteristics of MOFs)>

Regarding the MOFs synthesized for each of the Examples and Comparative Examples, after pre-treatment of each, the water vapor adsorption isotherm was measured to find the humidity at which water vapor adsorption is 30% (desorption humidity) and the humidity at which water vapor adsorption is 70% (adsorption humidity) when the water vapor adsorption under a relative humidity of 0 to 20% is taken as 100%. The pre-treatment device, pre-treatment conditions, measurement device and measurement conditions were as follows:

Pre-treatment device: BELPREP-vacII (MicrotracBEL Corp.)

Pre-treatment conditions: degree of vacuum<$10^{-2}$ Pa, heat at 130° C. for 6 hours Measurement device: BELSORP-max (MicrotracBEL Corp.)

Measurement conditions: measured amount of water vapor adsorbed at temperature 20° C., in a relative humidity of 0 to 85%

Figure 7:
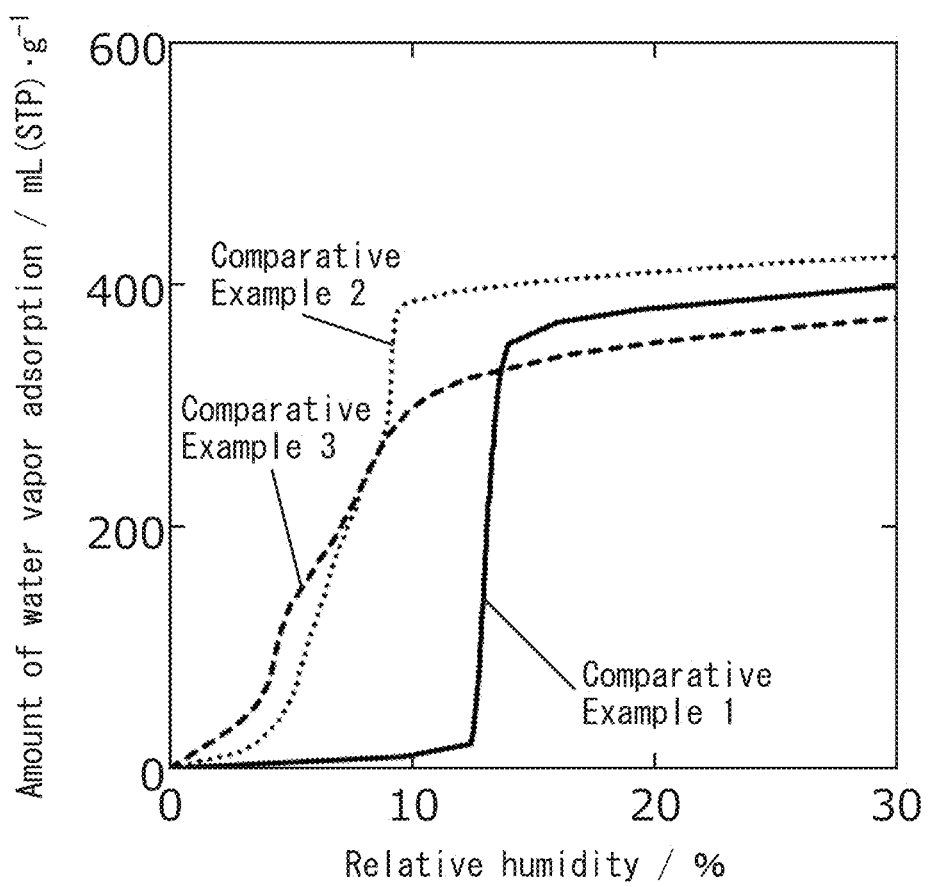
FIG. 7 is a graph showing the water vapor adsorption isotherms for the MOFs of Comparative Examples 1 to 3.
Figure 8:
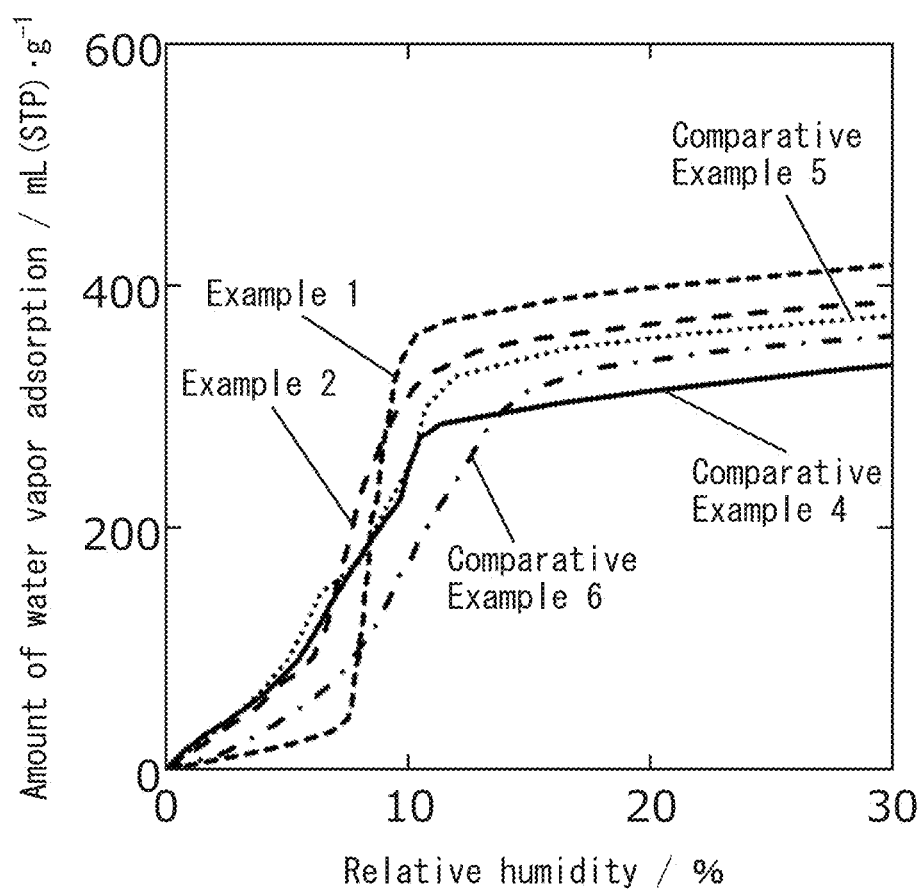
FIG. 8 is a graph showing the water vapor adsorption isotherms for the MOFs of Examples 1 and 2, and Comparative Examples 4 to 6.
Figure 9:
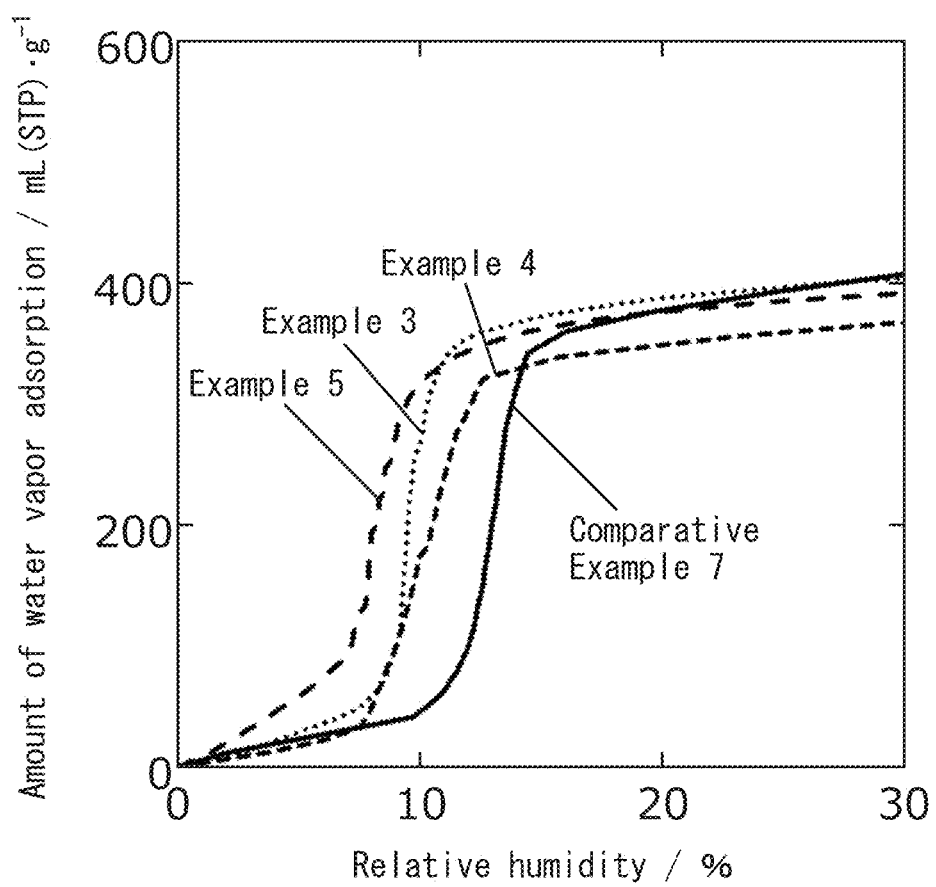
FIG. 9 is a graph showing the water vapor adsorption isotherms for the MOFs of Examples 3 to 5 and Comparative Example 7.
Figure 10:
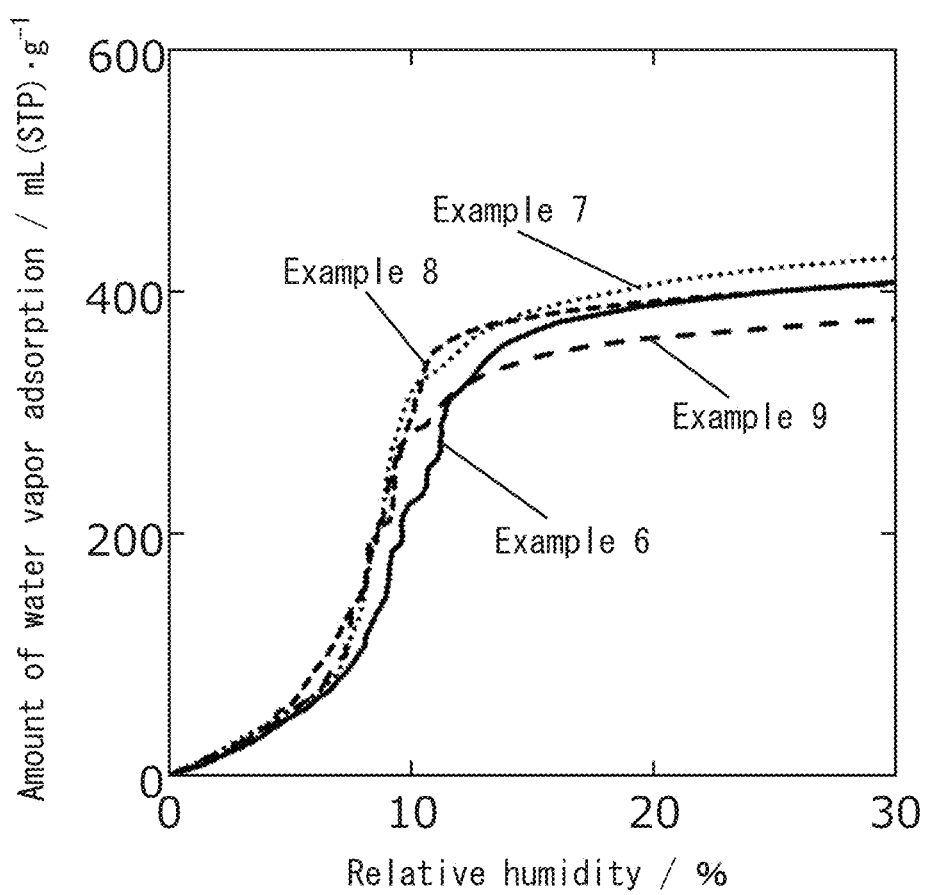
FIG. 10 is a drawing showing the water vapor adsorption isotherm for the MOFs of Examples 6 to 9.

FIGS. 1 and 7 to 10 show the water vapor adsorption isotherms measured for the MOFs synthesized for each of the Examples and Comparative Examples. More specifically, FIG. 1 shows the water vapor adsorption isotherms for the MOFs of Example 1, and Comparative Examples 1 and 3, FIG. 7 shows the water vapor adsorption isotherms for the MOFs of Comparative Examples 1 to 3, FIG. 8 shows the water vapor adsorption isotherms for the MOFs of Examples 1 and 2 and Comparative Examples 4 to 6, FIG. 9 shows the water vapor adsorption isotherms for the MOFs of Examples 3 to 5 and Comparative Example 7, and FIG. 10 shows the water vapor adsorption isotherms for Examples 6 to 9.

Figure 11:
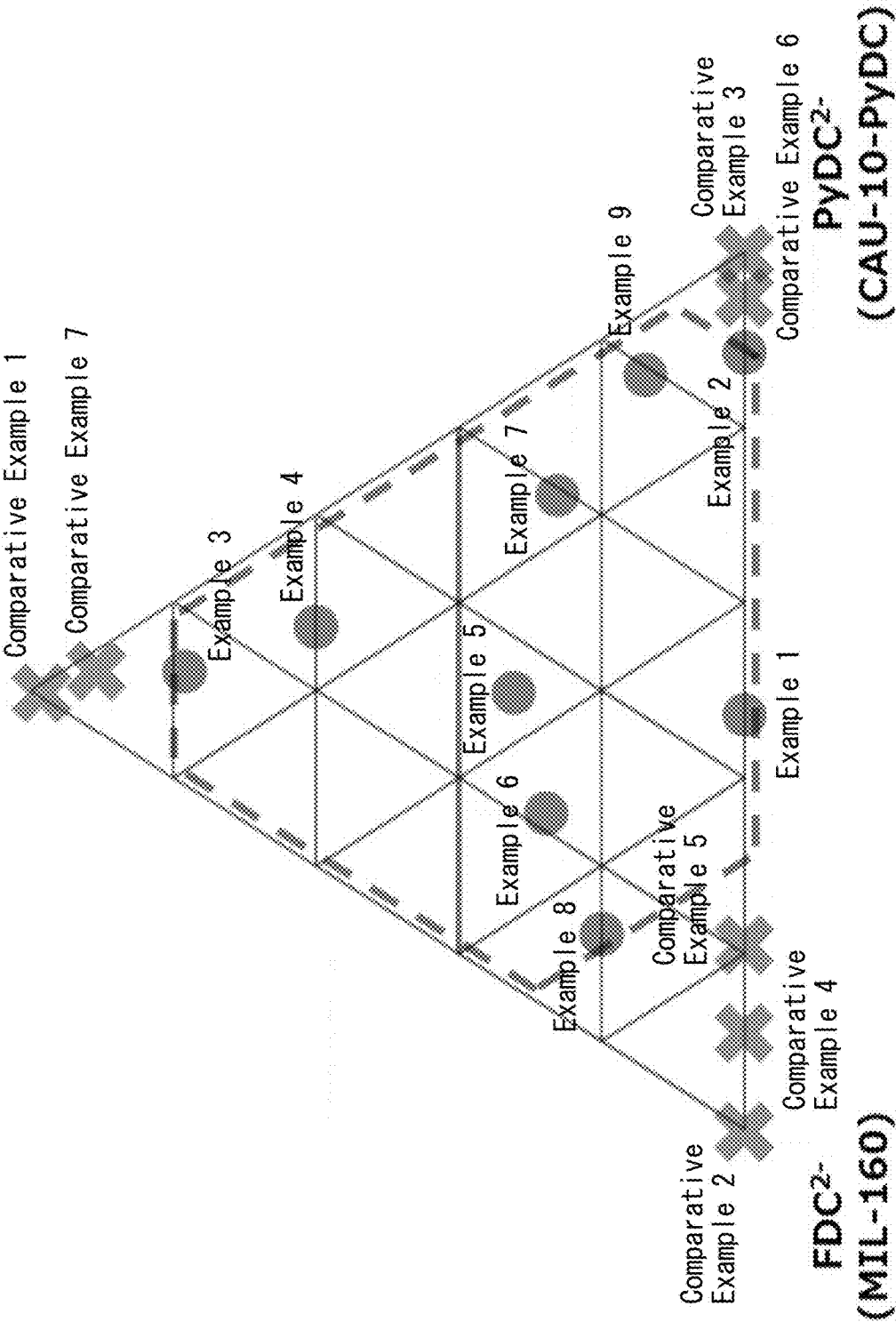
FIG. 11 is a drawing showing the composition ratios of the MOFs synthesized in the Examples and the Comparative Examples.
Figure 12:
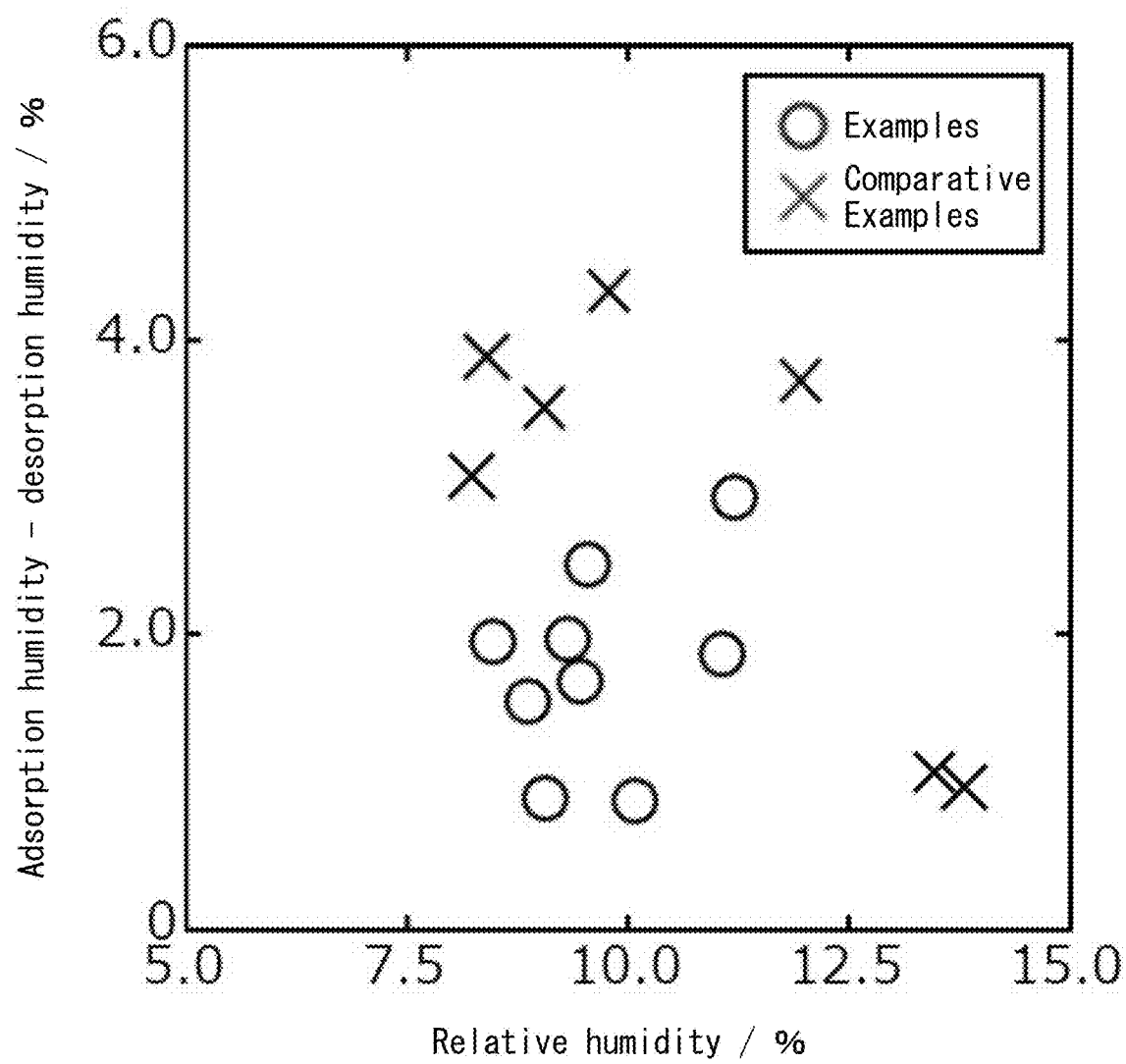
FIG. 12 is a drawing showing the correlation between the adsorption humidity of the MOFs synthesized in the Examples and the Comparative Examples with each of the humidity differences between the adsorption humidity and the desorption humidity.

Further, the results of analysis of the compositions of the MOFs synthesized for each of the Examples and the Comparative Examples and the results of evaluating the water vapor adsorption-desorption characteristics are shown in Table 2 below. For the sake of ease of comparison, the results of analysis of the composition of the MOFs synthesized for each of the Examples and Comparative Examples are shown in FIG. 11. Furthermore, as an example of water vapor desorption characteristics of the MOFs synthesized for each of the Examples and Comparative Examples, the relations between the adsorption humidities and the humidity differences between adsorption humidity and desorption humidity for each are shown in FIG. 12.

TABLE 2

| | Composition of contained ligand source | | | Result of analysis of ligand composition | | | Water vapor adsorption-desorption characteristics | | |
|---|---|---|---|---|---|---|---|---|---|
| | $H_2BDC$ (mol %) | $H_2FDC$ (mol %) | $H_2PyDC$ (mol %) | $BDC^{2-}$ (mol %) | $FDC^{2-}$ (mol %) | $PyDC^{2-}$ (mol %) | 1)Desorption humidity (%) | 2)Adsorption humidity (%) | 2) − 1) (%) |
| Comparative Example 1 | 1.00 | 0.00 | 0.00 | 1.00 | 0.00 | 0.00 | 13.0 | 13.8 | 0.9 |
| Comparative Example 2 | 0.00 | 1.00 | 0.00 | 0.00 | 1.00 | 0.00 | 5.9 | 8.2 | 3.1 |
| Comparative Example 3 | 0.00 | 0.00 | 1.00 | 0.00 | 0.00 | 1.00 | 4.5 | 8.4 | 3.9 |
| Comparative Example 4 | 0.00 | 0.90 | 0.10 | 0.00 | 0.87 | 0.13 | 5.5 | 9.0 | 3.5 |
| Comparative Example 5 | 0.00 | 0.80 | 0.20 | 0.00 | 0.79 | 0.21 | 5.4 | 9.8 | 4.3 |
| Example 1 | 0.00 | 0.50 | 0.50 | 0.00 | 0.54 | 0.46 | 8.1 | 9.0 | 0.9 |
| Example 2 | 0.00 | 0.20 | 0.80 | 0.00 | 0.11 | 0.89 | 6.5 | 8.5 | 1.9 |
| Comparative Example 6 | 0.00 | 0.10 | 0.90 | 0.00 | 0.06 | 0.94 | 8.2 | 11.9 | 3.7 |
| Comparative Example 7 | 0.80 | 0.10 | 0.10 | 0.92 | 0.02 | 0.06 | 12.4 | 13.4 | 1.1 |
| Example 3 | 0.60 | 0.20 | 0.20 | 0.78 | 0.08 | 0.14 | 9.2 | 10.1 | 0.9 |
| Example 4 | 0.40 | 0.30 | 0.30 | 0.60 | 0.14 | 0.26 | 9.2 | 11.1 | 1.9 |
| Example 5 | 0.20 | 0.40 | 0.40 | 0.34 | 0.33 | 0.33 | 7.3 | 8.8 | 1.5 |
| Example 6 | 0.20 | 0.60 | 0.20 | 0.32 | 0.47 | 0.22 | 8.3 | 11.2 | 2.9 |
| Example 7 | 0.20 | 0.20 | 0.60 | 0.28 | 0.14 | 0.58 | 7.8 | 9.4 | 1.7 |
| Example 8 | 0.10 | 0.80 | 0.10 | 0.21 | 0.66 | 0.13 | 7.1 | 9.5 | 2.5 |
| Example 9 | 0.10 | 0.10 | 0.80 | 0.16 | 0.07 | 0.78 | 7.3 | 9.3 | 2.0 |

«Evaluation of Results»

As can be understood from FIGS. 4 to 6, the target MOF was successfully synthesized for each of the Examples and Comparative Examples.

As is clear from Table 2 and FIG. 12, the MOFs of the Examples all had adsorption humidities of not more than 11.5%, and had differences between adsorption humidity and desorption humidity (adsorption humidity-desorption humidity) of not more than 3.0%. Thus, the MOFs of the present disclosure were able to simultaneously achieve both adsorption of water vapor at a low relative humidity and reducing of the size of the humidity difference between adsorption humidity and desorption humidity.

In contrast, for example, the MOFs of Comparative Examples 2 to 5 each had adsorption humidity of not more than 11.5%, but had differences between the adsorption humidity and the desorption humidity (adsorbed humidity-desorbed humidity) of not less than 3.1%. Additionally, MOFs of Comparative Examples 1 and 7 had differences between the adsorption humidity and the desorption humidity (adsorbed humidity-desorbed humidity) or not more than 1.1%, which is relatively small, but had adsorption humidities of not less than 13.4%. Thus, the MOFs of the Comparative Examples were not able to achieve both adsorption of water vapor at a low relative humidity and a reduction in the magnitude of the humidity difference between adsorbed humidity and desorbed humidity.

REFERENCE SIGNS LIST

10 water reservoir
20, 25 desiccant holder
30 water vapor channel
32 air supply channel
34 air extraction channel

What is claimed is:

1. A metal-organic framework comprising a metal ion, a first ligand, a second ligand, and an optional third ligand, wherein
   the metal ion is an aluminum ion,
   the first ligand is an organic compound ion consisting of a first heterocycle having two carboxyl groups, and a heteroatom composing the first heterocycle is present in the first ligand on the minor angle side of the angle created by the two carboxyl groups,
   the second ligand is an organic compound ion different from the first ligand and having two carboxyl groups, and a heteroatom composing the second heterocycle is present in the second ligand on the major angle side of the angle created by the two carboxyl groups,
   the third ligand is an organic compound ion different from the first ligand and the second ligand and having two carboxyl groups, and
   relative to the total of the first ligand, the second ligand, and the third ligand,
   the first ligand is present in a percentage of more than 0 mol % to 70 mol %,
   the second ligand is present in a percentage of more than 0 mol % to 90 mol %,
   and the third ligand is present in a percentage of 0 mol % to 80 mol %.

2. The metal-organic framework of claim 1, wherein the first heterocycle is a 5-membered ring or a 6-membered ring, and the second heterocycle is a 5-membered ring or a 6-membered ring.

3. The metal-organic framework of claim 1, wherein the first heterocycle is a 5-membered ring, and the second heterocycle is a 6-membered ring.

4. The metal-organic framework of claim 1, wherein
   the first ligand is a 2,5-furandicarboxylate ion,
   the second ligand is a 3,5-pyridinecarboxylate ion, and
   the third ligand is an isophthalate ion.

5. The metal-organic framework of claim 1, wherein the metal-organic framework has an adsorption humidity of not more than 11.5% and a difference between the adsorption humidity and a desorption humidity (adsorption humidity-desorption humidity) of not more than 3.0%, where the adsorption humidity is a humidity at which the amount of water vapor adsorbed is 70%, and the desorption humidity is a humidity at which the amount of water vapor adsorbed is 30%, when the amount of water vapor adsorbed at a relative humidity of 0 to 20% is taken to be 100%.

6. A chemical heat pump having the metal-organic framework of claim 1 as a desiccant.

7. A humidity control system having the metal-organic framework of claim 1 as a desiccant.

* * * * *